United States Patent [19]

Sioshansi et al.

[11] Patent Number: 5,133,757
[45] Date of Patent: Jul. 28, 1992

[54] ION IMPLANTATION OF PLASTIC ORTHOPAEDIC IMPLANTS

[75] Inventors: Piran Sioshansi, Bedford; Richard W. Oliver, Acton, both of Mass.

[73] Assignee: Spire Corporation, Bedford, Mass.

[21] Appl. No.: 560,837

[22] Filed: Jul. 31, 1990

[51] Int. Cl.$^5$ .............................................. A61F 2/30
[52] U.S. Cl. .................................................... 623/18
[58] Field of Search ............................ 623/18, 16, 66

[56] References Cited

U.S. PATENT DOCUMENTS

| | | | |
|---|---|---|---|
| 4,526,832 | 7/1985 | Bernett et al. | 427/38 X |
| 4,554,208 | 11/1985 | MacIver et al. | 427/38 X |
| 4,693,760 | 9/1987 | Sioshansi | 623/16 |
| 4,743,493 | 5/1988 | Sioshansi et al. | 428/217 |
| 4,944,754 | 7/1990 | Linkow et al. | 623/16 |

OTHER PUBLICATIONS

Gerhard K. Wolf, "Chemical Properties of Ion Implanted Materials", Treatise on Materials Science & Technology, (1980), pp. 373-414.

M. S. Dresselhaus et al., "Ion Implant. of Polymers", Mat. Res. Soc. Symp. Proc., vol. 27, (1984), pp. 413-422.

Pehr E. Pehrsson, et al., "Chem. & Phys. Interactions in Covalent Polymers Implanted w/Trans. Mets.", Mat. Res. Soc. Symp. Proc., vol. 27 (1984), pp. 429-434.

N. C. Koon et al., "Magnet. Prop. of Ion Implanted Polymers & Graphite", Mat. Res. Soc. Symp. Proc., vol. 27, (1984), pp. 445-448.

Piran Sioshansi, "Ion Beam Mod. of Materials for Industry", Thin Solid Films, 118, (1984), pp. 61-71.

M. L. J. Beck et al., "The Mechanism of Ion Implant. Passivation of PMMA . . . w/Dry Etch Develop.", Microelectronic Engineering, (1985), 451-458.

R. M. Ross et al., "Exploratory Investigations on the Structure Dependence of Wear Resist. of Polyethylene", Wear, 77, (1972), pp. 89-104.

R. M. Rose et al., "On Pressure Depend. of Wear of Ultrahigh Molec. Weight Polyethylene", Wear, 92, (1983), pp. 99-111.

R. M. Rose et al., "Radiation Sterilization & the Wear Rate of Polyethylene", Journal of Orthopaedic Research, 2:393-400.

I. C. Clarke et al., "Wear of Ti-6A1-4V Impl. Alloy & Ultrahigh Molec. Wt. Polyethylene Combinations".

Primary Examiner—David Isabella
Assistant Examiner—G. Gualtieri
Attorney, Agent, or Firm—Morse, Altman, Dacey & Benson

[57] ABSTRACT

A load-bearing plastic orthopaedic joint implant, formed aat least partially of UHMWPE or HDPE material, and a process of subjecting at least the load-bearing surface thereof to ion implantation so as to improve its surface characteristics are disclosed. Such improved surface characteristics result, inter alia, from the formation in the treated surfaces, of increased carbon to carbon bonds, diamond-like carbon chain scissions and wherein the implanted ions do not form precipitate chemical compounds with the plastic material.

6 Claims, 4 Drawing Sheets

ION IMPLANTATION OF PLASTIC ORTHOPAEDIC IMPLANTS

BACKGROUND OF INVENTION

1. Field of the Invention

The present invention relates generally to ion implantation of plastic orthopaedic implants and, more particularly, to a load-bearing orthopaedic joint implant partially or wholly formed of UHMWPE material and to a process for subjecting a load-bearing surface thereof to ion implantation so as to improve its surface characteristics.

2. The Prior Art

The present invention is an improvement over a previous invention of the applicants disclosed in U.S. Pat. No. 4,743,493, ION IMPLANTATION OF PLASTICS, granted May 10, 1988 and assigned to a common assignee, Spire Corporation of Bedford, Mass.

As stated in said U.S. Pat. No. 4,743,493, ion implementation is a method that was originally developed in the semiconductor industry to effect precise doping of silicon wafers with impurities. From there, the method spread to the ion implantation of metals and compounds, see *Treatise on Materials Science and Technology*, Vol. 18, "Ion Implantation," 1980, Academic Press, Inc. See also a copending application, assigned to the common assignee herein, entitled "Ion Implantation of Titanium Workpieces Without Surface Discoloration", Serial No. 861,845, filed May 12, 1986.

In the specific area of ion implantation of plastics, in the beginning most of the interest and research has focused on advantageously changing the electronic and transport properties of a variety of polymers that are normally insulating. By using masks, for instance, conducting paths in an insulating medium are fabricated. See the article authored by M.S. Dresselhaus et al of M.I.T. "Ion Implantation of Polymers," *Mat. Res. Soc. Symp. Proc.*, Vol. 27 (1984), pp. 413–422. Other workers in the field have studied the reaction of iodine ions with solid alkanes and the effect of carbon ions on benzene. See 7th Int. Hot Atom Chem. Symp. (1973) p. 19, and R. M. Lemmon, id., p. 20. Similar work in organometallic compounds, such as metal carbonyls, has indicated that energetic ions, such as copper and chromium, as well as rare-earth ions, interact with such compounds and that about half of the incoming ions become incorporated in the organometallic chain. See G. K. Wolf, "Ion Bombardment Chemistry," *Nucl. Instrum. Methods* 139 (1976) 147.

Our said previous invention, disclosed in said U.S. Pat. No. 4,743,493, primarily and principally dealt with the ion implantion of plastics, such as used as transparencies in aircraft, safety glasses and face masks, eyeglasses and contact lenses, or non-transparent plastics, such as used in bearings or safety helmets, so as to enhance their surface hardness or their resistance to chemical attack.

In biomedical applications, polyethylenes find important uses, inter alia, as acetabular cups in joint replacements, against which a metal part, lately formed of a titanium alloy or a CoCr alloy, known as F-75 alloy, is designed to bear. As known, the material of choice for the vast majority of total joint replacements is Ultrahigh Molecular Weight Polyethylene (UHMWPE) articulating against a mating surface formed of a Ti-6A1-4V alloy. Note R.M. Rose et al., "Exploratory Investigations on the Structure Dependence of the Wear Resistance of Polyethylene," *Wear*, 77 (1982), pp. 89–104; R.M. Rose et al., "On the Pressure Dependence of the Wear of Ultrahigh Molecular Weight Polyethylene," *Wear*, 92 (1983), pp. 99–111; R.M. Rose et al., "Radiation Sterilization and the Wear Rate of Polyethylene," *Journal of Orthopaedic Research*, 2: 393–400; and I.C. Clarke et al., "Wear of Ti-6A1-4V Implant Alloy and Ultrahigh Molecular Weight Polyethylene Combinations," *Titanium Alloys in Surgical Implants*. ASTM, STP 796 (1983), p. 136.

Until recently, difficulties of bone attachment and of body rejection have overshadowed and eclipsed wear rate in joint replacements. Advancements in technology have, however, effectively dealt with both bone attachment and body rejection. These improvements have, therefore, refocussed attention on the wear rate of UHMWPE, being now the primary cause of premature failure of an implanted joint prosthesis, requiring its premature replacement.

SUMMARY OF THE INVENTION

It is a principal object of the present invention to overcome the above disadvantages by providing an improved ion implantation process for a load-bearing plastic orthopaedic joint implant formed at least partly of UHMWPE and/or HDPE material and the product so formed.

More specifically, it is an object of the present invention to provide a process of ion implanting a load-bearing orthopaedic joint implant formed, at least partially, of UHMWPE material in order to improve its surface characteristics. At least a load-bearing surface of the UHMWPE material is implanted with an atomic concentration of about 0.01 to about 2 per cent and preferably below one per cent of an implanted ion species, with the depth of penetration not exceeding about two microns, and with the ion implanted load-bearing surface exhibiting, inter alia, increased carbon to carbon bonds, an improved microhardness for polyethylenes from about 3.5 to about 7.0 KHN at a one gram load, (KHN—Knoop Hardness Number, it denotes the relative microhardness of a material as determined by the Knoop indentation test, which is a diamond pyramid hardness test employing the Knoop indenter, with the hardness being determined by the depth of penetration of a tested surface), a coefficient of friction not exceeding about 0.1, an amorphous content of at least about 10%, and is characterized by reduced crystallinity. The process essentially comprises forming an orthopaedic implant at least partially from an UHMWPE material, mounting the implant in a chamber, creating a vacuum of about $10^{-6}$ torr therein, exposing a load-bearing surface of the implant formed of UHMWPE material to an ion beam to improve its surface characteristics, backfilling the chamber with an inert gas to about atmospheric pressure, and removing the ion implanted implant from the chamber. Preferably, the implant is subjected to heating prior to ion implantation as well as to quenching following implantation and removal from the chamber. Preferably, the backfilling is maintained for a time period of at least about one hour but not exceeding about five hours. Preferably, the orthopaedic implant is exposed to sterilization by gamma rays after the completion of the invention process. Preferably, the implanted ions include nitrogen, argon, helium, neon, aluminum, magnesium, silicon, titanium, fluorine and chlorine ions.

Other objects of the present invention will in part be obvious and will in part appear hereinafter.

The invention accordingly comprises the process and the resultant product of the present disclosure, its components, parts and their interrelationships, the scope of which will be indicated in the appended claims.

BRIEF DESCRIPTION OF THE DRAWINGS

For a fuller understanding of the nature and objects of the present invention, reference is to be made to the following detailed description, which is to be taken in connection with the accompanying drawings, wherein.

DETAILED DESCRIPTION OF THE PREFERRED EMBODIMENT

As mentioned, the present invention represents an improvement of the inventors' prior invention disclosed in U.S. Pat. No. 4,743,493, entitled ION IMPLANTATION OF PLASTICS, issued May 10, 1988 and assigned to the common assignee, Spire Corporation of Bedford, Mass., the disclosure of which is incorporated herein by reference.

As stated therein, ion implantation is designed to materially enhance the surface characteristics of the plastics, in particular by increasing their surface hardness and their resistance to chemical attack. The present invention specifically pertains to load-bearing plastic orthopaedic implants, formed at least in part of ultra high molecular weight polyethylene (UHMWPE) material and/or high density polyethylene (HDPE) material, and an improved process of subjecting at least the load-bearing surface thereof to ion implantion by ion species such as argon, helium, neon, nitrogen, aluminum, magnesium, silicon, titanium, yttrium, fluorine and chlorine ions.

Ultra high molecular weight polyethylenes (UHMWPE) and high density polyethylenes (HDPE, which are medium to high molecular weight polyethylenes) find important uses, among others, in orthopaedics as implants, such as in artificial knee, hip, shoulder, ankle, elbow, finger and toe replacements.

As mentioned, the process of the invention has been developed as a further attempt at improving the surface characteristics of a plastic load-bearing surface of orthopaedic joint implants formed at least partially of UHMWPE material. The improved surface characteristics include, inter alia, increased carbon to carbon bonds, with diamond-like carbon chain scission in the treated surface, wherein the implanted ions do not form precipitate chemical compounds with the implanted plastic material.

Figure 1:
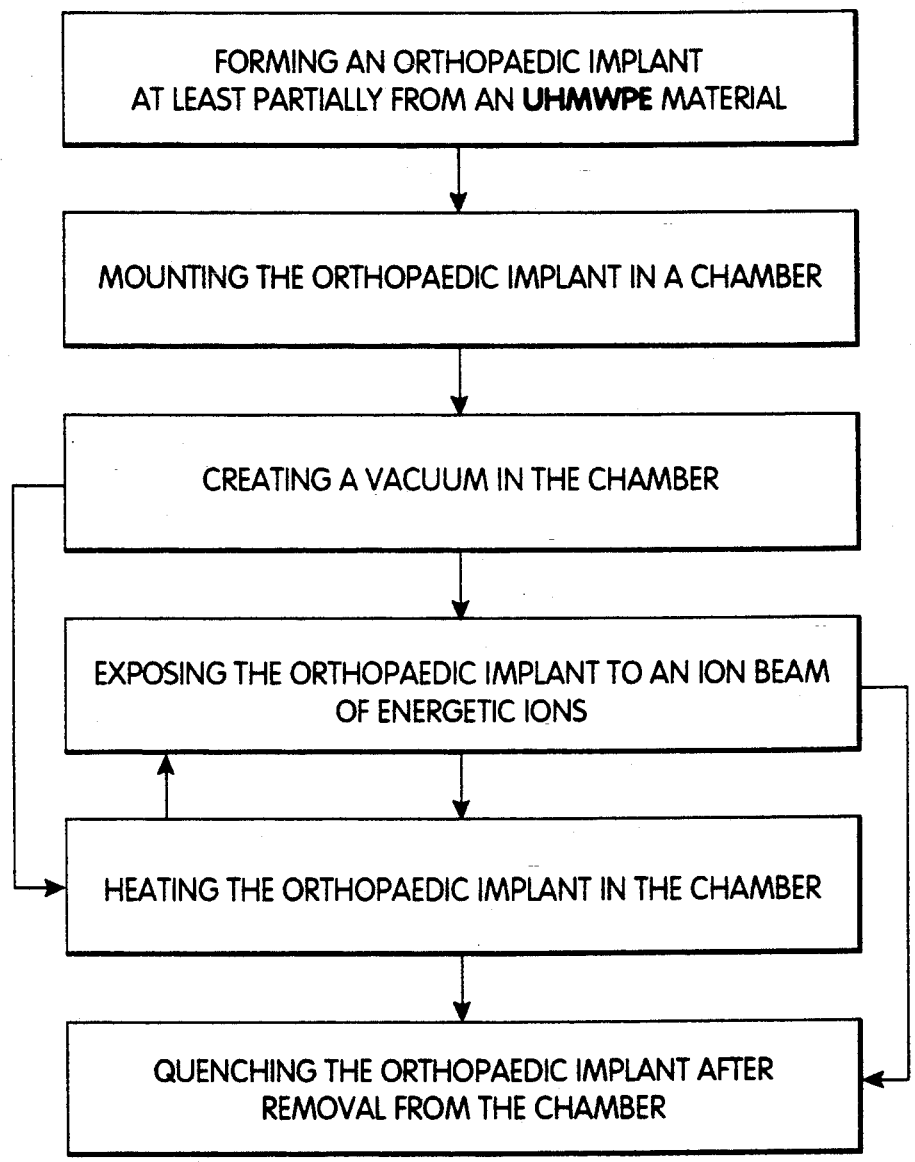
FIG. 1 is a flow diagram illustrating graphically the steps of the process of the invention.

Essentially, the process of the invention is graphically illustrated in FIG. 1. A plastic workpiece, formed as an orthopaedic implant at least partially from an UHMWPE or HDPE material is mounted in a suitable chamber, a vacuum is created within the chamber, and the plastic workpiece is exposed to an ion beam of an implantable ion species, such as, for example, at least a member of the class comprising aluminum, magnesium, silicon, titanium, argon, helium, neon, nitrogen, fluorine and chlorine ions, and the like. Preferably, the plastic workpiece is heated in the chamber by any convenient means prior to it being exposed to the ion implantation. Preferably, following the ion implantation, the chamber is backfilled with an inert gas to about atmospheric pressure for a predetermined time period from about one to about five hours. Also preferably, following the removal of the implanted workpiece from the chamber, the workpiece is quenched in any convenient and known manner. The ion implantation process of the invention improves the surface characteristics of the plastic workpieces by physically and chemically altering a thin surface stratum of the workpiece without changing the bulk properties thereof.

Representative load-bearing plastic orthopaedic joint implants, ion implanted according to the process of the invention, are illustrated in FIGS. 3-11. The thickness of the implanted layer of the joint implants can vary anywhere from about 0.01 micrometer to about five micrometers, and for the most part, is less than about two micrometers.

The energetic ions preferably are ion implanted into the plastic surface so as to achieve a Gaussian distribution therein. These ion implanted energetic ions contribute to increase its microhardness from about 3.5 to about 7.0 KHN at a one gram load. The doses required for the ion implantation of the plastic surfaces are quite low when compared to those used for metal surfaces (of the order from about $1 \times 10^{13}$ to about $1 \times 10^{16}$ ions per $cm^2$). Consequently, the atomic concentration of the implanted ion species is from about 0.01 to about two per cent and preferably is less than one per cent. This low percentage of atomic concentration of the implanted ion species rules out, for the most part, any adverse effects of any chemical compounds being precipitated in the implanted surface as a result of the ion implantation. The ion implanted energetic ions effect radiation damage within the plastic layer so as to cross link with certain of the polymer chains of the plastic material.

Figure 12:
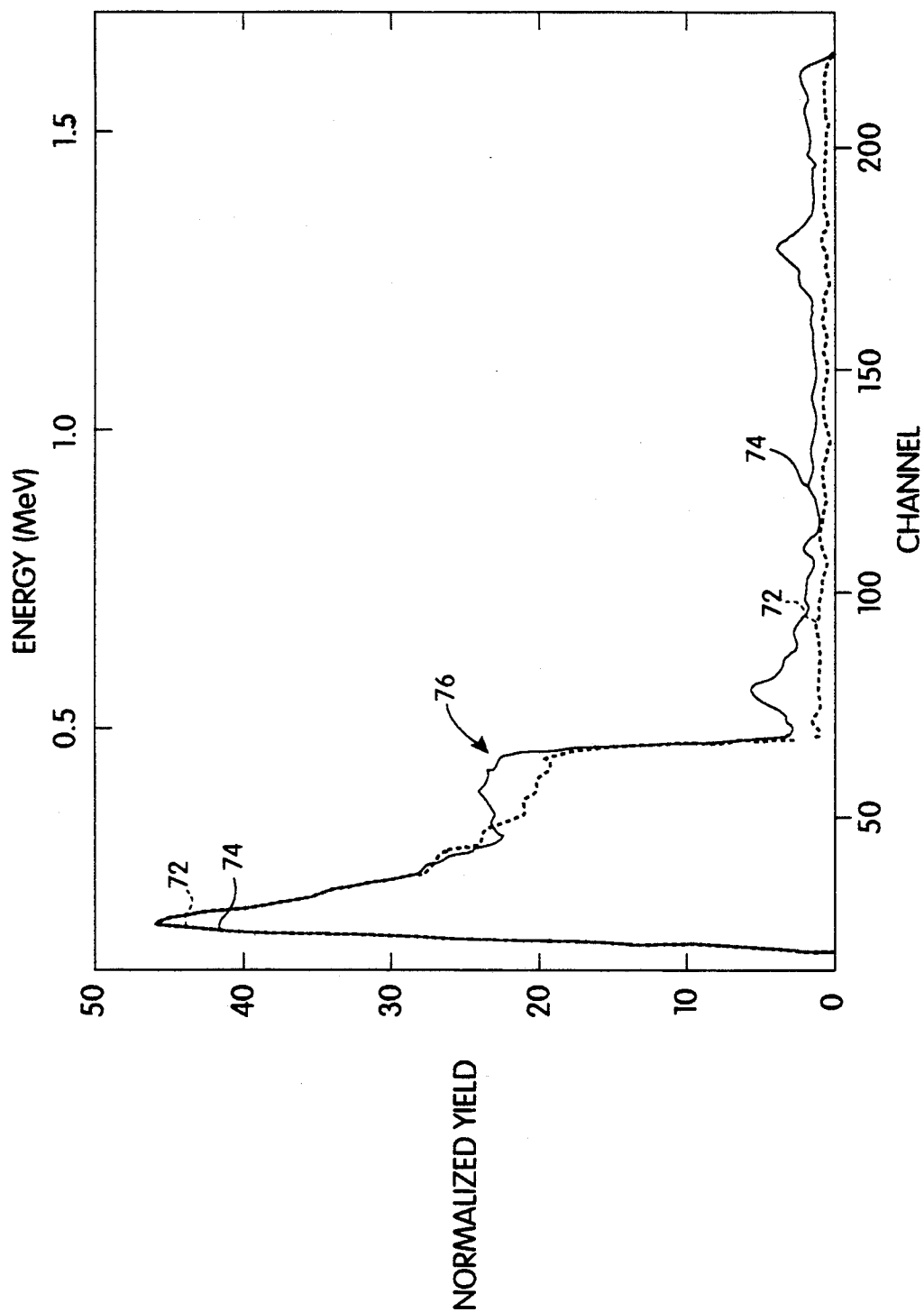
FIG. 12 is a schematic diagram helpful in understanding the invention.

FIG. 12 illustrates the effects of ion implantation with titanium on polyethylenes, in particular on UHMWPE, and contrasts it with a sample which was not ion implanted. There is shown a curve 72 of dots, representing the non ion-implanted sample and, a solid curve 74, representing the UHMWPE sample which has been ion-implanted according to the invention. These curves 72 and 74 plot the normalized yield per channel and represent data obtained by Rutherford back scattering (RBS). Arrow 76 points to an increased signal level for the ion-implanted polyethylene, clearly indicating the densification of the near surface region due to the presence of increased carbon to carbon bonds, with diamond-like carbon chain scission in the ion-implanted surface.

The ion implanted energetic ions thus contribute: to the formation of densification in the treated surface due to the presence of increased carbon to carbon bonds therein, with diamond-like carbon chain scission in the treated surface; to increase the microhardness of the implanted surface; to decrease the surface energy at the implanted surface, rendering it more hydrophobic; to increase the resistance to chemical attack; and to effect radiation damage, crosslinking thereby with certain of the polymer chains of the plastic material.

Figure 2:
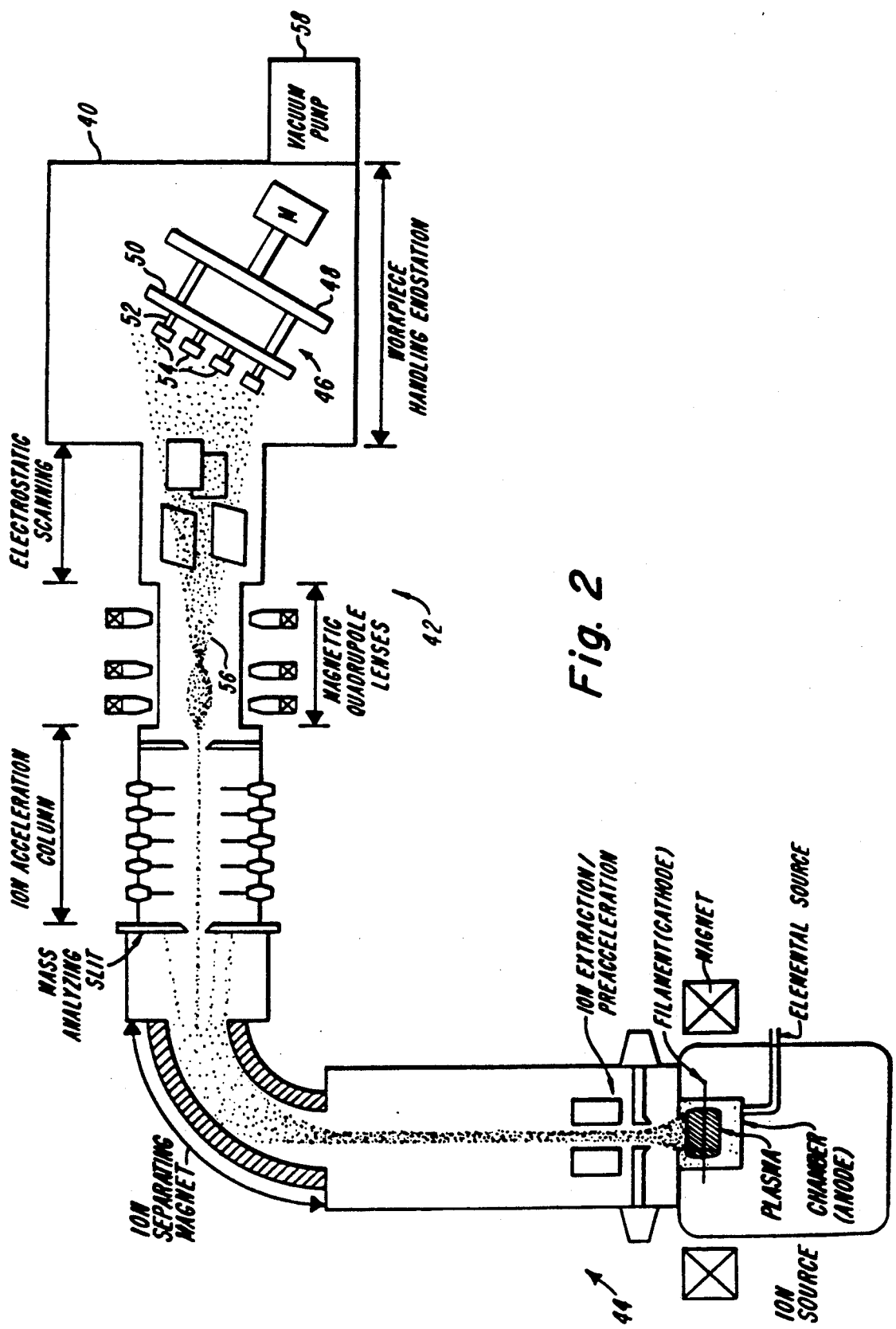
FIG. 2 is a schematic view of an ion beam implanter adapted to practice the steps of the process of the invention.
Figure 3:
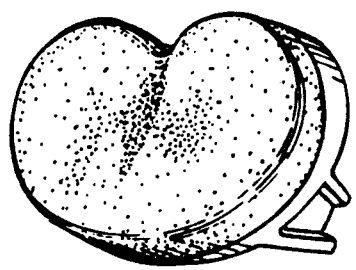
FIG. 3 is a perspective view of a plastic molded tibial component of a knee prosthesis.

The process of ion implanting the workpieces, including the orthopaedic implants illustrated in FIGS. 3 through 11, is preferably carried out in a suitable implant chamber 40 of a specially designed endstation 42 of a suitable high current ion implanter 44, such as a Varian-Extrion 200 kV implanter, an Eaton-Nova implanter or a like instrument, illustrated in FIG. 2. This ion implanter 44 can be the same as, or an adaptation of the one illustrated in and described in said U.S. Pat. No. 4,743,493 and assigned to the common assignee.

Within the implantation chamber 40, a suitable fixture 46 is mounted on a base 48 designed for rotation by a suitable motor (M) and for cooling a base plate 50, preferably made of titanium, by means not shown. On the base plate 50 are mounted a plurality of appropriately shaped workpiece holders 52, preferably made of aluminum. These workpiece holders 52 are designed to hold securely a plurality of plastic workpieces 54 and directly to expose these workpieces 54 to an incoming ion beam 56 of ions. The illustrated workpieces 54 are any one of the orthopaedic implants illustrated in FIGS. 3 through 11. It is to be understood that the shape of the particular workpiece holders 52 secured to the base plate 50 will of course depend upon the shape of the particular workpieces 54 worked on at that time.

With the plastic workpieces 54 duly mounted within the chamber 40, the next step of the process of the invention involves the creation of a proper vacuum environment within the implantation chamber 40. This is effected by means of a vacuum pump 58 operatively connected to the chamber 40. With the aid of the pump 58, the implantation chamber 40 is preferably evacuated to a vacuum pressure of about $10^{-6}$ torr. Preferably, the vacuum pump 58 should be of an oil-free type so as to avoid the possibility of introducing surface contamination onto the part to be ion implanted.

Preferably, the plastic workpieces 54 also are heated in any convenient manner either before or during the pump-down of the chamber 40 to a temperature of about 50° to about 70° C. and then are maintained at that temperature. The plastic workpieces 54 are then exposed to the ion beam 56 so as to modify their surface characteristics. Preferably, the ion beam possesses an energy from about 20 to about 400 keV, delivering a dose from about $1 \times 10^{13}$ to about $1 \times 10^{16}$ per square centimeter. The abovementioned ion beam energy and ion dose are intended to achieve a current density on the respective surfaces of the workpieces 54 from about 0.1 microampere per square centimeter to about one microampere per square centimeter. The ion implantation process of the invention is effected over a time period from about one half to about four hours, depending on the desired hardness to be achieved by a selected combination of ion dose and ion beam current. It has been observed that both dose and ion beam current density, as measured by the delivered dose of ions on the surfaces of the workpieces, has a darkening effect on the plastic material, especially in the region of the visible light spectrum between about 4,000 and about 6,000 Angstroms. This darkening effect preferably is used for process verification and/or quality control. Ion implantation results in a reduced coefficient of friction of about 0.1. It is believed that the discoloration of plastics is due to localized heat generation of the ions as they slow down and stop in the plastic and can be eliminated by using a less intense ion beam (lower current density). By spreading the ion beam 56 over a larger area and consequently lowering the current density at the plastic material's surface, the degree of darkening of the plastics can be effectively controlled.

EXAMPLE I

Figure 4:
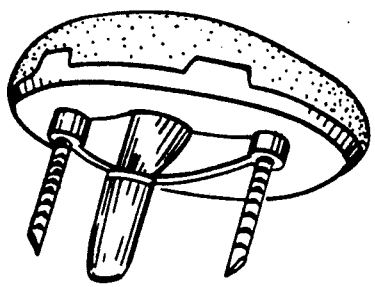
FIG. 4 is a perspective view of another tibial component formed at least partially of UHMWPE material.
Figure 5:
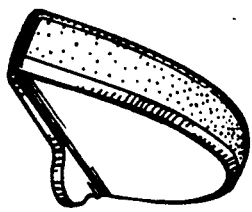
FIG. 5 is a perspective view of another plastic molded tibial component designed for a partial knee prosthesis.
Figure 6:
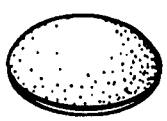
FIG. 6 is a perspective view of an all plastic molded patellar component of a knee prosthesis.
Figure 7:
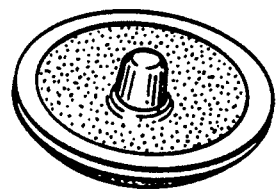
FIG. 7 is a perspective view of a metal-reinforced plastic molded patellar component.
Figure 8:
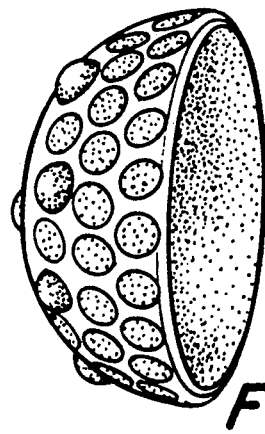
FIG. 8 is a perspective view of a metallic component of an acetabular cup of a hip prosthesis.

An orthopaedic implant, such as the one disclosed in FIG. 4, which is a metal-reinforced tibial component of a knee prosthesis, was ion implanted in the implant chamber 40, employing the following implant parameters:

Ion species: Ti
Energy of ion beam: 160 KeV
Dose of ions delivered per $cm^2$: 1 E 15
Current density on the implanted surface per $cm^2$: 500 nanoamps
Time period of implantation: 1 hour
Atomic concentration of the implanted ion species: one %.
Depth of penetration of the implanted ion species: 0.2 micron

EXAMPLE II

Figure 9:
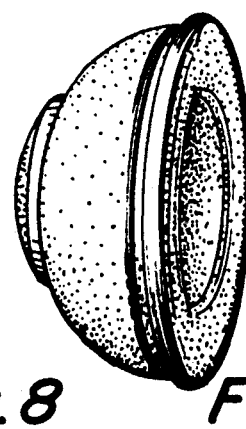
FIG. 9 is a perspective view of a plastic component of the acetabular cup of FIG. 8.
Figure 10:
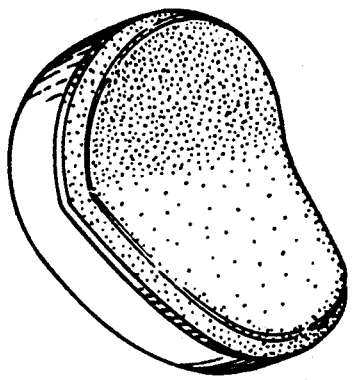
FIG. 10 is a perspective view of a metal-backed plastic molded glenoid component of a shoulder prosthesis.
Figure 11:
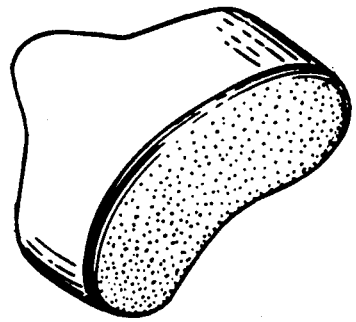
FIG. 11 is a perspective view of an all plastic molded glenoid component.

An orthopaedic implant, such as the all-plastic acetabular cup disclosed in FIG. 9, which is a component of a hip prosthesis, was ion implanted in the implant chamber 40, employing the following implant parameters:

Ion species: Argon
Multiple energy implant: first, at 160 KeV, delivering a dose per $cm^2$ of 2.7 E 15, followed by a dose of 2.7 E 15 at 130 KeV, a dose of 2.7 E 15 at 100 KeV, a dose of 2.7 E 15 at 70 KeV, and finally a dose of 2.7 E 15 at 45 KeV, resulting in a
Total dose of ions delivered per $cm^2$: 1.35 E 16
Current density on the implanted surface per $cm^2$: 1.25 microamps
Time period of implantion: 1 hour
Atomic concentration of the implanted ion species: about 2%
Depth of penetration of the implanted ion species: 0.25 micron Thus it has been shown and described a process for the ion implantation of load-bearing plastic orthopaedic joint implants with ions designed to improve their surface characteristics, notably their surface hardness and their resistance to chemical attack, which process and resultant product satisfy the objects and advantages set forth above.

Since certain changes may be made in the present disclosure without departing from the scope of the present invention, it is intended that all matter described in the foregoing specification or shown in the accompanying drawings, be interpreted in an illustrative and not in a limiting sense.

What is claimed is:

1. A process of ion implanting a load-bearing plastic orthopaedic joint implant comprising:
   (a) forming an orthopaedic implant at least partially from an UHMWPE or HDPE material;
   (b) mounting said implant in a chamber;
   (c) creating a vacuum of about $10^{-6}$ torr in said chamber;
   (d) exposing a surface of said implant formed of said UHMWPE or HDPE material to an ion beam to improve its surface characteristics, in particular by increasing the carbon to carbon bonds therein, with diamond-like carbon chain scission in said exposed surface;
   (e) backfilling said chamber with an inert gas to about atmospheric pressure wherein said backfilling step is maintained for a time period of at least about one hour and not exceeding about five hours so as to effect formation of said carbon to carbon bonds of said ion implanted surface; and
   (f) removing said ion implant from said chamber.

2. The process of claim 1 further including heating said implant in said chamber prior to exposing said surface thereof to said ion beam; and further including quenching said implant following its said removal from said chamber.

3. The process of claim 1 wherein said plastic orthopaedic implant is sterilized by gamma rays after the implant is removed from the chamber; and wherein said ion implanted exposed surface has been implanted with an atomic concentration from about 0.01 to about 2 percent of said ion beam.

4. A process of ion implanting a load-bearing plastic orthopaedic joint implant comprising:
   (a) forming an orthopaedic implant at least partially from an UHMWPE or HDPE material;
   (b) mounting said implant in a chamber;
   (c) creating a vacuum of about $10^{-6}$ torr in said chamber;
   (d) exposing a surface of said implant formed of said UHMWPE or HDPE material to an ion beam to effect ion implantation thereof at multiple energies so as to improve its surface characteristics; said exposing step resulting in a total dose of ions delivered per $cm^2$ of about 1.35 E 16; and an atomic concentration of the implanted ion species of about 2%;
   (e) backfilling said chamber with an inert gas to about atmospheric pressure; and
   (f) removing said ion implant from said chamber;

5. The process of claim 4 wherein said plastic orthopaedic implant is exposed to sterilization by gamma rays after the implant is removed from the chamber, wherein the depth of penetration of the implanted ion species is about 0.25 micron, and wherein said exposing step effects said surface in about one hour.

6. The process of claim 4 wherein a current density of said ion implanted surface per $cm^2$ is about 1.25 microamps.

* * * * *

UNITED STATES PATENT AND TRADEMARK OFFICE
CERTIFICATE OF CORRECTION

PATENT NO. : 5,133,757

DATED : July 28, 1992

INVENTOR(S) : Piran Sioshansi and Richard W. Oliver

It is certified that error appears in the above-identified patent and that said Letters Patent is hereby corrected as shown below:

In column 1, after the title, please insert the following clause:

-- This invention was made with Government support under grant "1R43AR38802-01A2" awarded by the National Institutes of Health. The government has certain rights in the invention. --

Signed and Sealed this

Twenty-first Day of September, 1993

Attest:

BRUCE LEHMAN

*Attesting Officer*   *Commissioner of Patents and Trademarks*